United States Patent [19]
Saito et al.

[11] Patent Number: 5,219,855
[45] Date of Patent: Jun. 15, 1993

[54] ANXIOLYTIC DRUG

[75] Inventors: Ken-Ichi Saito, Machida; Akihiro Tobe, Yokohama; Heitaro Iwata, Ibaraki; Akemichi Baba, Nishinomiya; Toshio Matsuda, Settsu, all of Japan

[73] Assignee: Mitsubishi Kasei Corporation, Tokyo, Japan

[21] Appl. No.: 839,737

[22] Filed: Feb. 19, 1992

Related U.S. Application Data

[63] Continuation of Ser. No. 442,332, Jan. 7, 1989, abandoned.

[30] Foreign Application Priority Data

Jan. 29, 1988 [JP] Japan .................. 63-19055

[51] Int. Cl.$^5$ ................. A61K 31/495; A61K 31/505; A61K 31/415
[52] U.S. Cl. .................... 514/252; 514/269; 514/397; 514/406
[58] Field of Search .............. 514/252, 233.2, 228.5, 514/247, 269, 357, 406

[56] References Cited

U.S. PATENT DOCUMENTS

| | | | |
|---|---|---|---|
| 4,202,898 | 5/1980 | Depoortere | 514/255 |
| 4,590,193 | 5/1986 | Creuzet et al. | 514/253 |
| 4,668,681 | 5/1987 | Pontagnier et al. | 514/255 |
| 4,889,852 | 12/1989 | Hartog et al. | 514/230.5 |
| 4,937,245 | 6/1990 | Fex et al. | 514/252 |
| 5,034,390 | 7/1991 | Olsson et al. | 514/252 |
| 5,128,343 | 7/1992 | Pinol et al. | 514/252 |

FOREIGN PATENT DOCUMENTS

| | | |
|---|---|---|
| 0175541 | 2/1986 | European Pat. Off. . |
| 56-5462 | 1/1981 | Japan . |
| 1166595 | 10/1990 | United Kingdom . |

OTHER PUBLICATIONS

"J. Med. Chem." 11 (6) pp. 1151-1155 (1968).
Acta Pharmaceutica Sinica, vol. XVI, No. 5, May 1981, p. 327; Z. Gang et al.; "Neuropharmocological sctions of some N-phenyl-piperszine derivatives".

*Primary Examiner*—Frederick E. Waddell
*Assistant Examiner*—T. J. Criares
*Attorney, Agent, or Firm*—David G. Conlin; Ernest V. Linek

[57] ABSTRACT

Disclosed herein are anxiolytic drugs containing as an active ingredient a piperazine derivative represented by the following general formula (I):

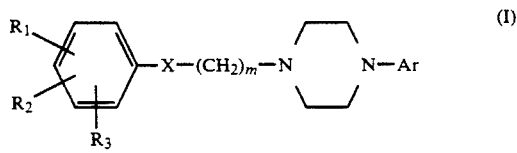

wherein
m represents an integer from 2 to 4,
X represents

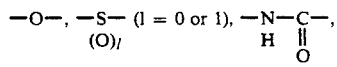

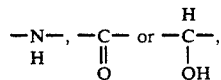

Ar represents a pyridyl group, a pyrimidinyl group, or a phenyl group which may be substituted with halogen atom, trifluoromethyl group, alkoxy group or alkyl group, and
$R_1$, $R_2$ and $R_3$ which may be identical or different represent lower alkoxy groups, or $R_3$ is a hydrogen atom and $R_1$ when taken together with $R_2$ forms

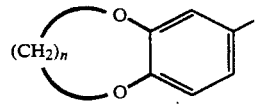

(n=1, 2 or 3);
and its acid addition salt.

The anxiolytic drugs disclosed herein have the high binding capacities to 5-HT$_{1A}$ receptor which is one of the receptors for 5-hydroxytryptamine (5-HT), thereby exerting anxiolytic effects.

1 Claim, No Drawings

ANXIOLYTIC DRUG

This is a continuation of copending application Ser. No. 07/442,332 filed on Nov. 7, 1989, now abandoned.

FIELD OF THE INVENTION

The present invention relates to an anxiolytic drug containing as an active ingredient a specified piperazine derivative and its acid addition salt.

BACKGROUND OF THE INVENTION

Benzodiazepine compounds have conventionally been known as anxiolytic drugs. Recently, Buspirone [N-(4-(4-(2-pyrimidinyl)-1-piperazinyl)butyl)-1,1-cyclopentanediacetamide hydrochloride] and other compounds have become recognized as new anxiolytic drugs with action mechanisms different from those of the benzodiazepines, but the advent of newer anxiolytic drugs is being desired.

Taking notice of the piperazine derivatives, the present inventors earnestly investigated to develop compounds which may be used as anxiolytic drugs. A variety of piperazine derivatives have been recognized to have a satisfactory antihypertensive effect (for example, Japanese Patent Application Laying-Open (KOKAI) No. 57-80379, No. 57-114588, No. 58-24563 and No. 58-154573, but were not known to have anxiolytic activities.

Now, the present inventors have discovered that certain piperazine derivatives and their acid addition salts have satisfactory anxiolytic effects, and thus the present invention has been completed.

DISCLOSURE OF THE INVENTION

The present invention relates to an anxiolytic drug containing as an active ingredient a piperazine derivative represented by the following general formula (I):

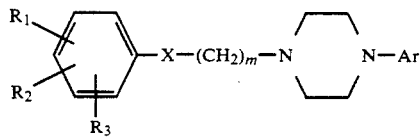

wherein
m represents an integer from 2 to 4,
X represents

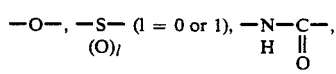

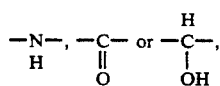

Ar represents a pyridyl group, a pyrimidinyl group, or a phenyl group which may be substituted with halogen atom, trifluoromethyl group, alkoxy group or alkyl group, and $R_1$, $R_2$ and $R_3$ which may be identical or different represent lower alkoxy groups, or $R_3$ is a hydrogen atom and $R_1$ when taken together with $R_2$ forms

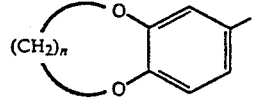

(N=1, 2 or 3) and its acid addition salt.

The present invention will be described in detail below. The piperazine derivatives used in the present invention are those represented by the above general formula (I).

The suitable compounds in the present invention are those represented by the above formula (I) wherein m represents 3, X represents —O—, —CO— or —CH(OH)—, Ar represents a pyridyl group or a phenyl group which may be substituted with any one of the above substituents, and $R_1$, $R_2$ and $R_3$ which may be identical or different represent $C_1$-$C_3$ lower alkoxy groups, or $R_3$ is a hydrogen atom and $R_1$ when taken together with $R_2$ forms

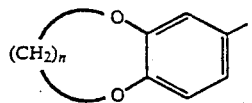

(n=1 or 2); and its acid addition salt.

The acid addition salt of the present invention may be formed with any inorganic acid such as hydrochloric acid, hydrobromic acid, sulfuric acid, phosphoric acid and nitric acid, or any organic acid such as acetic acid, succinic acid, adipic acid, propionic acid, tartaric acid, fumaric acid, maleic acid, oxalic acid, citric acid, benzoic acid, toluenesulfonic acid and methanesulfonic acid.

The above compounds may be easily synthesized, for example in accordance with the procedures described in Japanese Patent Application Laying-Open (KOKAI) No. 57-80379, No. 57-114588, No. 58-24563 and No. 58-154573.

For example Japanese Patent Application (Kokai) No. 57-80379 describes (omega-piperazinylalkoxy)alkylene dioxybenzenes and their acid addition salts represented by the general formula (IA):

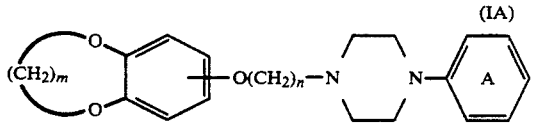

wherein:
m is an integer of 1 to 3;
n is an integer of 2 to 10;
A is phenyl which may have one or more substituents selected from the group of halogen, trifluoromethyl, alkoxy, alkylcarbonyl, alkyl and nitro.

The compounds according to this invention can be obtained by reacting halogenoalkoxyalkylene dioxybenzenes represented by the following formula (II):

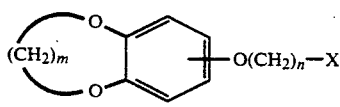

wherein m and n have the same meanings as in the general formula (IA) and X is halogen, with piperazines represented by the following formula (III):

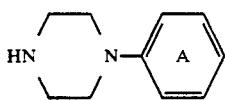

wherein A has the same meaning as in the general formula (IA).

The reaction of a halogenoalkoxyalkylene dioxybenzene with a piperazine can proceed in a ratio of 1:1, but generally the use of piperazine in excess is preferred so that the reaction proceeds smoothly. Typically from about 1 to 10 moles of piperazine per mole of halogenoalkoxyalkylene dioxybenzene is used.

The above reaction proceeds satisfactorily in the absence of solvents, but an inert solvent can be used for proceeding the reaction smoothly. Suitable inert solvents include water dioxane, tetrahydrofuran, dimethylformamide, dimethylsulfoxide, lower alcohol and their mixture.

The reaction temperature is not particularly limited. Generally, it is in the range from the room temperature to 150° C.

The reaction time may be varied depending on the reaction temperature, the reactivities of the starting compounds and the nature of the solvent used. Generally, it is in the range from 10 minutes to 20 hours.

For collecting the hydrogen halide produced during the reaction and for promoting the reaction, any base can be added. Examples of suitable bases include inorganic bases such as potassium hydroxide, potassium carbonate, sodium hydroxide, sodium hydrogen carbonate and sodium carbonate as well as tertiary organic amines such as pyridine and triethylamine. Generally, from 1 to 5 moles of base per mole of piperazine is used.

After the reaction is complete, excess amine and solvent are removed by distilling or washing with water and then an aqueous solution of a strong base such as sodium hydroxide or potassium hydroxide is added to form the free piperazinylalkoxyalkylene dioxybenzene, which is extracted with any solvent such as ether, chloroform, benzene and toluene. The desired acid is added so that its acid addition salt can be obtained.

Similarly, Japanese Patent Application (Kokai) No. 57-114588 describes (omega-piperazinylalkoxy)-alkylene dioxybenzenes and their acid addition salts represented by the general formula (IB):

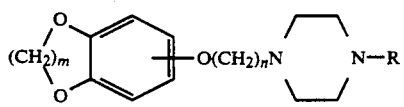

wherein
m is an integer of 1 to 3;
n is an integer of 2 to 10;
R is pyridyl, pyrazinyl, pyrimidinyl or pyridazinyl.

The compounds according to this invention can be obtained by reacting (halogenoalkoxy)alkylene dioxybenzenes represented by the formula (II):

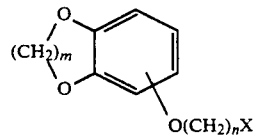

wherein m and n have the same meanings as in the general formula (IB) and X is halogen, with piperazines represented by the following formula (III):

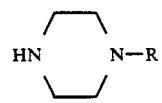

wherein R has the same meaning as in the general formula (IB).

The compounds according to this invention can be obtained by reacting (omega-piperazinylalkoxy)alkylene dioxybenzenes represented by the formula (IV):

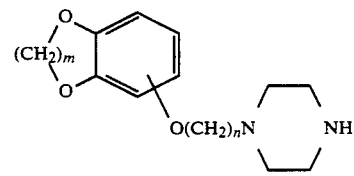

wherein m and n have the same meanings as in the general formula (IB), with halogeno compounds represented by the formula (V):

R—X           (V)

wherein R has the same meanings as in the general formula (IB) and X is halogen. The above (omega-piperazinylalkoxy)alkylene dioxybenzenes (IV) can be obtained by reacting (halogenoalkoxy)alkylene dioxybenzene with piperazines.

The reaction of a (halogenoalkoxy)alkylene dioxybenzene with a piperazine can proceed in a ratio of 1:1, but generally the use of piperazine in excess is preferable so that the reaction proceeds smoothly. Generally, from 1 to 10 moles of piperazine per mole of (halogenoalkoxy)alkylene dioxybenzene is used.

When an (omega-piperazinylalkoxy)alkylene dioxybenzene (IV) is reacted with a halogeno compound (V), from 1 to 3 moles of halogeno compound per mole of (omega-piperazinylalkoxy)alkylene dioxybenzene is used.

While the above reaction proceeds satisfactorily in the absence of solvents, an inert solvent can be used to help run the reaction smoothly. Suitable inert solvents include water, dioxane, tetrahydrofuran, dimethylformamide, dimethylsulfoxide, lower alcohol and their mixtures.

The reaction temperature is not particularly limited. Generally, it is in the range of from about room temperature to 150° C.

The reaction time may be varied depending on the reaction temperature, the reactivities of the starting compounds and the nature of the solvent used. Generally, the reaction time is in the range from about 10 minutes to 20 hours.

For collecting the hydrogen halide produced during the reaction and for promoting the reaction, any base can be added. Several examples of such bases include inorganic bases such as potassium hydroxide, potassium carbonate, sodium hydroxide, sodium hydrogen carbonate and sodium carbonate as well as tertiary organic amines such as pyridine and triethylamine. Generally, from 1 to 5 moles of base per mole of piperazine is used.

After the reaction is complete, excess amine and solvent are removed by distilling or washing with water and then an aqueous solution of a strong base such as sodium hydroxide or potassium hydroxide is added to form the free (omega-piperazinylalkoxy)alkylenedioxybenzene, which is extracted with a solvent such as ether, chloroform, benzene or toluene. The desired acid is added so that its acid addition salt can be obtained.

Likewise, Japanese Patent Application (Kokai) No. 58-24563 describes (omega-piperazinylalkoxy)polyalkoxy benzenes and their acid addition salts. In particular, this application describes (omega-piperazinylalkoxy)-polyalkoxybenzenes and their acid addition salts represented by the following general formula (IC):

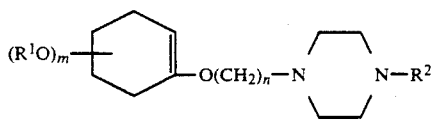
(IC)

wherein
m is an integer of 2 or 3;
n is an integer of 3 or 4;
$R^1$ is alkyl containing 1 to 3 carbon atoms;
$R^2$ is pyridyl, pyrazinyl, pyrimidyl or phenyl which may have one or more substituents selected from the group of halogen, trifluoromethyl, alkoxy and alkyl.

The compounds of this invention can be obtained by reacting halogenoalkyl polyalkoxybenzenes represented by the following formula (II):

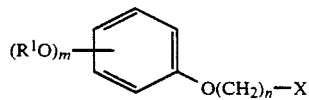
(II)

wherein $R^1$, m and n have the same meanings as in the general formula (IC) and X is halogen, with piperazine derivatives represented by the following formula (III):

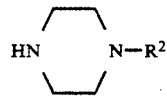
(III)

wherein $R^2$ has the same meaning as in the general formula (IC).

The reaction of a halogenoalkoxy polyalkoxybenzene with a piperazine derivative can proceed in a ratio of 1:1, but preferably, the piperazine derivative is used in excess, so that the reaction proceeds smoothly. From 1 to 10 moles of piperazine derivative per mole of halogenoalkoxy polyalkoxybenzene is typically used.

The above reaction proceeds satisfactorily in the absence of solvents, but an inert solvent can be used to ensure that the reaction proceeds smoothly. Suitable inert solvents include water, dioxane, tetrahydrofuran, dimethylformamide, dimethylsulfoxide, lower alcohols and their mixtures.

The reaction temperature is not particularly limited. Generally, it is in the range of from about room temperature to 150° C.

The reaction time may be varied depending on the reaction temperature, the reactivities of the starting compounds and the nature of the solvent used. Generally, it is in the range from 10 minutes to 20 hours.

For collecting the hydrogen halide produced during the reaction and promoting the reaction, any base can be added. Examples of suitable bases include inorganic bases such as potassium hydroxide potassium carbonate, sodium hydroxide, sodium hydrogen carbonate and sodium carbonate as well as tertiary organic amines such as pyridine and triethylamine, Generally, from 1 to 5 moles of base per mole of piperazine is used.

After the reaction is complete, excess amine and solvent are removed by distilling or washing with water and then, if necessary, an aqueous solution f a strong base such as sodium hydroxide or potassium hydroxide is added to form the free (omega-piperazinylalkoxy)-polyalkoxybenzene, which is extracted with a suitable solvent such as ether, chloroform, benzene or toluene. The desired acid is added so that its acid addition salt can be obtained.

Finally, Japanese Patent Application (Kokai) No. 58-154573 described alkylenedioxybenzene derivatives and their acid addition salts represented by the following formula (ID):

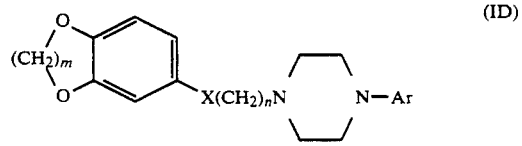
(ID)

wherein
m is an integer of 1 to 3;
n is an integer of 1 to 4;
X is selected from the group consisting of:

wherein l=0, 1, or 2;

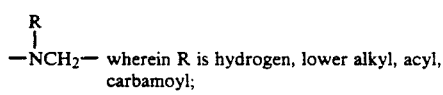

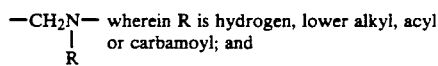

wherein Ar is pyridyl or phenyl which may be substituted with halogen, alkyl or alkoxy), provided that n is not 1 when X is —CONH— or

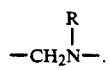

The compounds according to this invention can be obtained by reacting halogenoalkoxy alkylenedioxybenzene derivatives represented by the following formula (II):

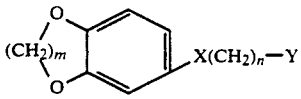
(II)

wherein m, n and X have the same meanings as in the general formula (ID) and Y is halogen, with amines represented by the following formula (III):

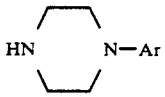
(III)

wherein Ar has the same meanings as in the general formula (ID).

The reaction of a halogenoalkoxy alkylenedioxybenzene derivative with an amine can proceed in a ratio of 1:1, but generally the use of the amine in excess is preferred so that the reaction proceeds smoothly. From 1 to 10 moles of amine per mole of halogenoalkoxy alkylene dioxybenzene derivative is typically used.

The above reaction proceeds satisfactorily in the absence of solvents, but an inert solvent can be used to ensure that the reaction proceeds smoothly. Suitable inert solvents include water, dioxane, tetrahydrofuran, dimethylformamide, dimethylsulfoxide, lower alcohols and their mixtures.

The reaction temperature is not particularly limited; generally, it is in the range of from about room temperature to 150° C. The reaction time may be varied depending on the reaction temperature, the reactivities of the starting compounds and the nature of the solvent used. Generally, it is in the range from about 10 minutes to 50 hours.

For collecting the hydrogen halide produced during the reaction and for promoting the reaction, any base can be added. The examples of suitable bases include inorganic bases such as potassium hydroxide, potassium carbonate, sodium hydroxide, sodium hydrogen carbonate and sodium carbonate as well as tertiary organic amines such as pyridine and triethylamine. Generally, from about 1 to 5 moles of the base per mole of amine is used.

After the reaction is complete, excess amine and solvent are removed by distilling or washing with water and then, an aqueous solution of a strong base such as sodium hydroxide or potassium hydroxide is added to form the free alkylenedioxybenzene derivative, which is extracted with a solvent such as ether, chloroform, benzene or toluene. The desired acid is added so that its acid addition salt can be obtained.

As the acid, any of the acids generally employed for the preparation of an acid addition salt of a compound can be used. For example, inorganic acids such as hydrochloric acid, hydrobromic acid, sulfuric acid, phosphoric acid and nitric acid as well as organic acids such as acetic acid, succinic acid, adipic acid, propionic acid, tartaric acid, fumaric acid, maleic acid, oxalic acid, citric acid, benzoic acid, toluenesulfonic acid and methanesulfonic acid are suitable.

The alkylenedioxybenzene derivative represented by the following formula (IV):

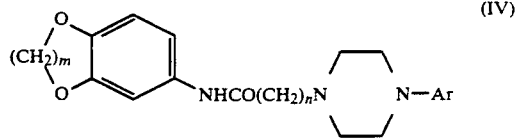
(IV)

wherein m, n and Ar have the same meanings as in the general formula (ID), which is prepared as above, is subjected to reduction by means of a metal hydride such as LiAlH₄ so as to obtain the alkylenedioxybenzene derivative represented by the following formula (V):

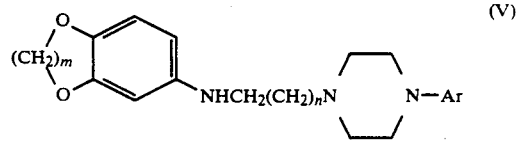
(V)

wherein m, n and Ar have the same meanings as in the general formula (ID).

In the same manner, the alkylenedioxybenzene derivative represented by the formula (VI) can also be obtained:

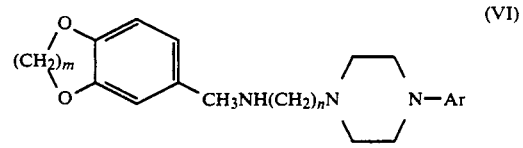
(VI)

The alkylenedioxybenzene derivative represented by the following formula (VII):

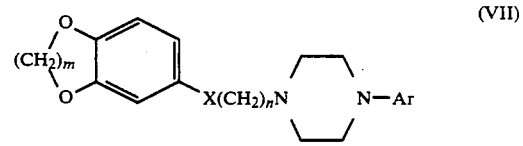
(VII)

wherein n, n and Ar have the same meanings as in the general formula (ID) and X is

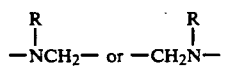

wherein R is lower alkyl containing 1 to 3 carbon atoms, acyl containing 1 to 3 carbon atoms or carbamoyl, can be obtained by treating the compound of formula (V) or (IV) with an alkanoic anhydride or halide in a basic solvent such as pyridine or in the presence of an inorganic base such as potassium carbonate, by treating an isocyanate salt in an acid solvent such as acetic acid, by treating with an alkyl halide in the presence of an organic base such as triethylamine or an inorganic base such as potassium carbonate, or by subjecting it to reductive alkylation by means of an aldehyde.

These alkylenedioxybenzene derivatives can be converted into their acid addition salts according to the manner described above.

The compounds of the present invention bind to 5-HT$_{1A}$ receptor which is one of the receptors for 5-hydroxytryptamine, as shown in the following Examples.

Compounds which bind to 5-HT$_{1A}$ receptor, for example, Buspirone [N-(4-(4-(2-pyrimidinyl)-1-piperazinyl)-butyl)-1,1-cyclopentadiacetamide hydrochloride] (Naunyn-Schmiedeberg's Arch. Pharmakol., 328, 467, 1985) and Ipsapirone [2-(4-(4-(2-pyrimidinyl)-1-piperazinyl)butyl)-1,2-benzisothiazol-3-(2H)one-1,1-dioxydehydrochloride] and SM-3997 [3aα, 4β, 7β, 7aα-hexahydro-2-(4-(4-(2-pyrimidinyl)-1-piperazinyl)butyl)-4,7-metano-1H-isoindole-1,3(2H)-dione dihydrogen citrate] (Naunyn-Schmiedeberg's Arch. Pharmakol., 328, 467, 1985; Japan. J. Pharmacol., 45, 493, 1987) have been known to exert an anxiolytic effect. The compounds of the present invention may be used as anxiolytic drugs based on their similar activities.

When intended for use as anxiolytic drugs, the compounds of the present invention may be administered through any routes. But, it is preferable to administer the anxiolytic drugs of the present invention parenterally including subcutaneous, intravenous, intramuscular or intraperitoneal injection, or orally.

The dosage is determined depending on age, health condition and body weight of the patient, type and frequency of combined treatment, if any as well as nature of desired effects, and so on.

Generally, the daily dosage of the active ingredient is 0.01 to 10.0 mg per kg body weight, usually 0.1 to 3 mg/kg body weight, in a single or divided administration.

For oral administration, the compounds of the present invention are used in the form such as tablets, capsules, powder, liquid, or elixir. And, for parenteral administration, they are used as sterilized liquids including suspensions. Solid or liquid, non-toxic pharmaceutical carriers may be included in the preparations of the present invention when used in any of the above dosage forms.

As an example of solid carrier, usual gelatin type capsules are used. And, the active ingredient may be formed into tablets or powder in combination with or without any additives.

These capsules, tablets and powder generally contain 5 to 95% by weight, preferably 25 to 90% by weight of the active ingredient.

That is, the preparations provided by the present invention advisably contain 5 to 500 mg, preferably 25 to 250 mg of the active ingredient for administration in these dosage forms.

As liquid carriers, water, oils of animal or plant origin such as petroleum oil, peanut oil, soybean oil, mineral oil and sesame oil, or synthetic oils may be used.

Furthermore, physiological saline solution, dextrose or similar sucrose solution, and glycols such as ethylene glycol, propylene glycol and polyethylene glycol are generally preferable as liquid carriers. Particularly in case of injection employing physiological saline, the injection is to be formulated so that the content of the active ingredient is usually 0.5 to 20% by weight, preferably 1 to 10% by weight.

Liquid preparations for oral administration may advisably be in the form of suspension or syrup containing 0.5 to 10% by weight of the active ingredient.

On these preparations, flavoring agents and aqueous excipients such as syrup and pharmaceutical micelles may be used as carriers.

PREFERRED EMBODIMENTS OF THE INVENTION

The present invention will now be illustrated by the following examples, but it is to be clearly understood that the description made in connection with these examples is only for the purpose of illustration and not as a limitation on the scope of invention.

EXAMPLE 1

The compounds of the present invention listed in Table 1 were synthesized by the conventional techniques and their affinities for 5-HT$_{1A}$ receptor were determined by a binding assay using 8-hydroxy-2-(di-n-propylamino) tetralin ([3H]8-OH-DPAT) which is a selective ligand for 5-HT$_{1A}$ receptor (Neuropharmacol., 26, 139, 1987). To say more exactly, a rat brain was homogenized in Tris buffer and centrifuged. The resultant sediment was rehomogenized using Tris buffer and incubated at 37° C. for 10 minutes, followed by centrifugation. The resulting deposit was homogenized in Tris buffer containing pargyline, calcium chloride and ascorbic acid and subjected to binding assay (membrane preparation).

The assay was carried out by combining the membrane preparation with [3H]8-OH-DPAT and the test compound and then incubating at 37° C. for 10 minutes.

Subsequently, the mixture was immediately filtered through a Whatman GF/B filter and the radio-activity remaining on the filter was measured by liquid chromatography.

The binding capacity of the test compound to 5-HT$_{1A}$ receptor was expressed as Ki value calculated by the formula:

$$Ki = \frac{IC_{50}}{1 + \frac{[L]}{kd}}$$

wherein [L] denotes the concentration of [3H]8-OH-DPAT, kd represents the dissociation constant, and IC$_{50}$ represents the concentration of the test compound required to produce a 50% inhibition of [3H]8-OH-DPAT binding. It is considered, therefore, that the lower the Ki value, the greater the potential usefulness of the test compound as an anxiolytic drug.

Results are shown in Table 1.

TABLE 1

Structure: R1,R2-substituted phenyl—X—(CH2)m—N(piperazine)N—Ar, with R3 substituent.

| No. | m | —R1, —R2 | —R3 | Substituted positions | X | —Ar | Addition salt | Ki value (nM) |
|---|---|---|---|---|---|---|---|---|
| 1 | 3 | methylenedioxyphenyl | H | — | —O— | phenyl | 2HCl | 4.7 |
| 2 | 3 | " | " | " | —O— | 2-pyridyl | 3HCl | 2.4 |
| 3 | 3 | " | " | " | —O— | 2-pyrimidinyl | 4HCl | 10.1 |
| 4 | 4 | " | " | " | —O— | phenyl | 2HCl | 10.1 |
| 5 | 4 | " | " | " | —O— | 4-F-phenyl | 2HCl | 33.2 |
| 6 | 4 | methylenedioxyphenyl | H | — | —O— | 3-CF3-phenyl | 2HCl | 55.9 |
| 7 | 3 | CH3O—, CH3O— | CH3O— | 3, 4, 5 | —O— | phenyl | HCl | 5.7 |
| 8 | 3 | CH3O—, CH3O— | H | 3, 4 | —O— | 2-OCH3-phenyl | 2HCl | 14.3 |
| 9 | 3 | CH3O—, CH3O— | " | 1, 5 | —O— | phenyl | 2HCl | 63.7 |
| 10 | 2 | methylenedioxyphenyl | " | — | —NC(=O)H— | phenyl | — | 25.4 |
| 11 | 3 | methylenedioxyphenyl | " | — | —NH— | phenyl | 3HCl | 18.0 |

TABLE 1-continued

R1,R2-phenyl-X-(CH2)m-N(piperazine)N-Ar with R3

| No. | m | —R₁, —R₂ | —R₃ | Substituted positions | X | —Ar | Addition salt | Ki value (nM) |
|---|---|---|---|---|---|---|---|---|
| 12 | 3 | 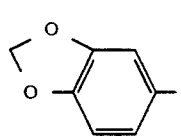 (methylenedioxy) | H | — | —O— | 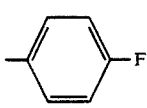 4-F-phenyl | 2HCl | 16.0 |
| 13 | 3 | " | " | " | —O— | 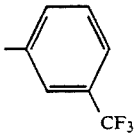 3-CF₃-phenyl | 2HCl | 8.0 |
| 14 | 3 | " | " | " | —O— | 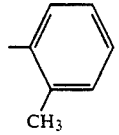 2-CH₃-phenyl | 2HCl | 101.0 |
| 15 | 3 | 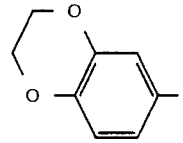 (ethylenedioxy) | " | " | —O— | 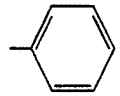 phenyl | 4HCl | 5.7 |
| 16 | 2 | 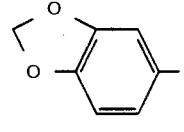 (methylenedioxy) | " | " | —O— | 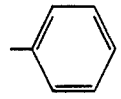 phenyl | 2HCl | 127.2 |
| 17 | 3 | " | " | " | —C(=O)— | 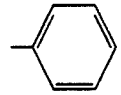 phenyl | 2HCl | 5.7 |
| 18 | 3 | 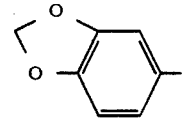 (methylenedioxy) | H | — | —CH(OH)— | 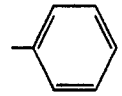 phenyl | 2HCl | 8.0 |
| 19 | 4 | 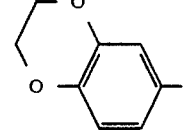 (ethylenedioxy) | " | " | —O— | 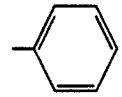 phenyl | 2HCl | 16.0 |
| 20 | 4 | 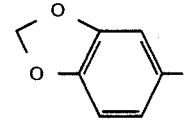 (methylenedioxy) | " | " | —C(=O)— | 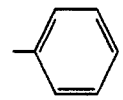 phenyl | 2HCl | 10.1 |

TABLE 1-continued

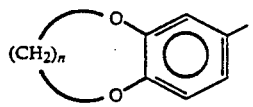

| No. | m | —R$_1$, —R$_2$ | —R$_3$ | Substituted positions | X | —Ar | Addition salt | Ki value (nM) |
|---|---|---|---|---|---|---|---|---|
| 21 | 3 | (benzodioxole) | " | " | —S— | phenyl | — | 71.2 |
| 22 | 3 | (benzodioxane) | " | " | —S(=O)— | phenyl | — | 25.4 |
| Reference | | | | | Buspirone | | | 14 |
| Reference | | | | | Ipsapirone | | | 2.2 |

AVAILABILITY IN INDUSTRY

The compounds of the present invention have proven to have a binding capacity to 5-HT$_{1A}$ comparable to or even greater than that of the known anxiolytic drugs, Buspirone and Ipsapirone, and accordingly, may be used as anxiolytic drugs based on the same action as that of the known drugs.

Furthermore, the compounds of the present invention may have marked usefulness as anxiolytic drugs with a high degree of safety because they are less liable to cause the side effects such as drowsiness and muscle relaxation which are observed in the use of the benzodiazepine compounds which are conventional anxiolytic drugs.

We claim:

1. A method of treating anxiety in patients in need of such treatment which comprises administering to said patients an anxiolytically effective amount of a piperazine derivative represented by the formula (I):

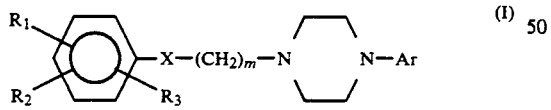
(I)

wherein
m represents an integer from 2 to 4,

X is selected from the group consisting of:

—O—, —S(O)$_l$— (wherein $l$ = 0 or 1),

—N(H)—, —C(=O)—, or —C(H)(OH)—,

Ar represents a pyridyl group, a pyrimidinyl group, or a phenyl group, each of which may be substituted with a radical selected from the group consisting of halogen, trifluoromethyl, lower alkoxy, or lower alkyl, and R$_1$, R$_2$ and R$_3$ which may be identical or different represent lower alkoxy groups, or R$_3$ is a hydrogen atom and R$_1$ when taken together with R$_2$ forms (benzo-fused dioxa ring with (CH$_2$)$_n$)

wherein n = 1, 2 or 3;
and its acid addition salts; wherein the anxiolytic activity of said piperazine derivative is based upon the binding capability thereof to the 5-HT$_{1A}$ receptor.

* * * * *

UNITED STATES PATENT AND TRADEMARK OFFICE
CERTIFICATE OF CORRECTION

PATENT NO. : 5,219,855

DATED : June 15, 1993

INVENTOR(S) : Saito et al.

It is certified that error appears in the above-identified patent and that said Letters Patent is hereby corrected as shown below:

On the title page: Item [63] change "Jan.7, 1989" to --Nov. 7, 1989 --.

Signed and Sealed this

Twenty-second Day of March, 1994

Attest:

BRUCE LEHMAN

*Attesting Officer*         *Commissioner of Patents and Trademarks*